United States Patent [19]

Ellison

[11] Patent Number: 5,177,827
[45] Date of Patent: Jan. 12, 1993

[54] ELECTRIC-POWERED DENTAL BRUSH

[76] Inventor: Benedict M. Ellison, Box-881555, San Diego, Calif. 92168

[21] Appl. No.: 640,604

[22] Filed: Jan. 14, 1991

[51] Int. Cl.$^5$ ............................................. A61C 17/26
[52] U.S. Cl. ......................................... 15/22.1; 15/23
[58] Field of Search ........................... 15/23, 24, 22.1; 128/62 A

[56] References Cited

U.S. PATENT DOCUMENTS

| | | | |
|---|---|---|---|
| 3,447,178 | 6/1969 | Pickering | 15/24 |
| 3,551,932 | 1/1971 | Grossman | 15/23 |
| 3,800,350 | 4/1974 | Francolino | 15/23 |
| 3,925,841 | 12/1975 | Callendo | 15/23 |
| 4,224,710 | 9/1980 | Solow | 15/22.1 |
| 4,237,574 | 12/1980 | Kelly et al. | 15/22.1 |
| 4,304,023 | 12/1981 | O'Rourke | 15/23 |
| 4,313,237 | 2/1982 | Smith | 15/23 |
| 4,538,315 | 9/1985 | Barth | 15/23 |
| 4,603,448 | 8/1986 | Middleton | 15/22.1 |

Primary Examiner—Edward L. Roberts
Attorney, Agent, or Firm—Berry, Dunbar, Daniel, O'Connor & Jordan

[57] ABSTRACT

Providing the user with a simplified single-procedure approach to self-administered dental-care, achieved through means of a special hand-portable/battery-powered instrument, having a rechargeable-battery and a motor with gear-reduction contained within the handle portion. While preferably detachably-mounted thereto is a special extensile bifurcated structure, provided with lateral adjustability by which to accomodate variations in individual mouth width, while supporting a plurality of motor-driven rotary-brush elements capable of uniformly scrubbing all of the mouth's teeth, away from the gums, inside and out, in a simultaneous single motion fully-automated manner. Hence, the notion of a manually inserted, selectively actuated oral instrument, serving to brush clean the entire inside mouth surfaces of the gums, teeth, and adjoining cheek and tongue surfaces in a rapid simultaneous manner being a substantial advancement, efficiently eliminating reliance upon one's own manual dexterity for effectual daily oral-hygiene.

3 Claims, 1 Drawing Sheet

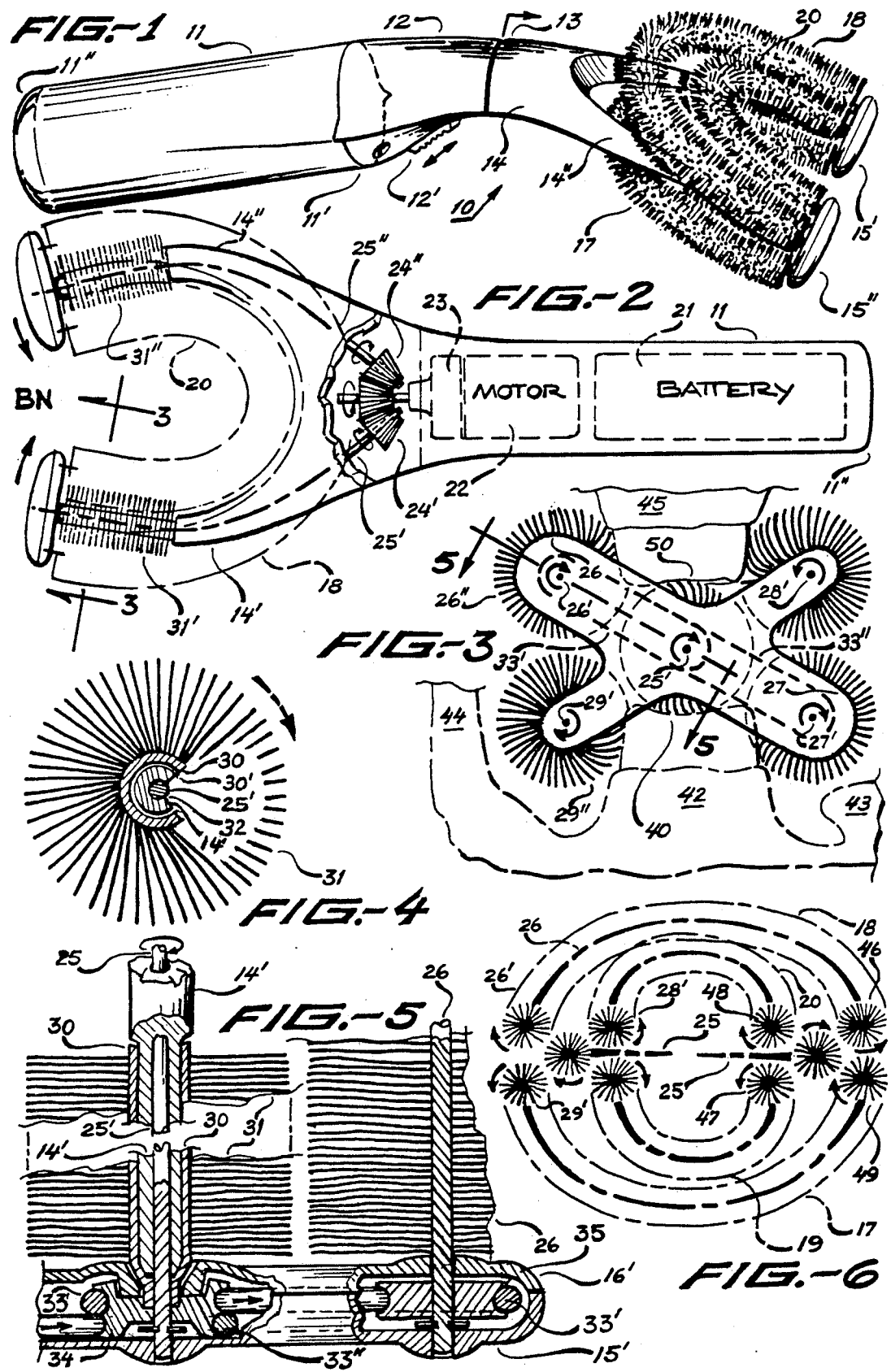

ELECTRIC-POWERED DENTAL BRUSH

BACKGROUND OF THE INVENTION

This invention relates to non-oscillating rotary-brush type electric toothbrushes having handle integrated battery, motor, gear-reduction, and electrical-control members arranged thereto; and more particularly it relates to such units having radial-brush elements, and specifically to such devices capable of brushing a substantial number of one's teeth in one motion of the user's hand. Accordingly, while there is no known brush invention of this sort which can facilitate brushing of the entire dental array in a single "one shot" manner, the following discussion addresses the most relevant related invention art known.

Beginning then with U.S. Pat. No. 3,447,178 (filed January/1968), a pistol-grip configuration is shown having a cylindrically formed distally positioned radial-brush member, plus a special toothpaste injector means. In retrospect however, it's primary virtue appears to lay in it's early approach to more extensive brushing of either the jaw or cranial dental array in one insertion/-motion; albeit less than ideally human-engineered.

Next, U.S. Pat. No. 3,551,932 endeavors to provide an electrically reversible radial-brush wherein is included a snap-apart shaft support-housing, for ease of cleaning. In U.S. Pat. No. 3,829,922 (filed January/1973) we see where this inventor has provided a special automatic reversing-switch mechanism, wherein FIG. 8 shows how the switch enables the inside and outside of the teeth/gum surfaces to be thus more effectively brushed away from the gum and up upon the teeth, so as to act to draw foreign matter out of the gum crevices interjacent to the teeth.

Perhaps most significantly, U.S. Pat. No. 3,924,841 (filed March/1974) introduced a toothbrush having a driving mechanism geared to a plurality of six coacting radial type rotary-brushes capable of brushing outward from the root area of either the jaw or the cranial teeth. These six brushes are hence geared to a motor-pinion & ring arrangement, so as to thereby stem off toward the right and left lateral sides in a rather Y-shaped formation; the battery, motor, and gear-housing being at the base of this arrangement. Critical to this layout is the need for a relatively rigid supporting structure, which is not at all really addressed in this invention disclosure. Thus, it is believed the difficulty of providing a suitable non-bulky bifurcated supporting-structure was apparently never actually revealed; hence, accounting for such a product never known to appear on the marketplace as a viable dental-care instrument.

Later, U.S. Pat. No. 4,313,237 (filed March/1980) revealed a drive related to the previous example, although somewhat less dynamic an implementation; since instead of brushing the entire jaw or cranial dental array simultaneously, the triad rotary-brush assembly is an entity in of itself, wherein FIG. 6 demonstrated the same brushing action set forth in FIG. 3 of the previous identified patent, as well as a still earlier example of U.S. Pat. No. 2,628,377 (issued February/1953).

Several other newer radial type rotary-brush patent examples have since issued to the present moment, yet they are essentially all of the single rotating-brush element design, stressing use of substantial manual dexterity by the user in determining both the extent of time-dwell needed in the different dental areas of the mouth, and the proper positioning of the brushing instrument in order to achieve optimal cleaning action.

Accordingly, this instant disclosure now intends to reveal how a fully automated arrangement of radial/rotary-brush elements may be regarded as advancement over the known invention art of record. Presently, this subject invention is being developed under auspices of the Xplak-toothbrush Co., San Diego, Calif.

SUMMARY OF THE INVENTION a.) the primary object of this subject invention is to virtually eliminate the rather hit-and-miss proceedual brushing techniques generally employed by the average individual, while utilizing any of the electric-toothbrush devices currently available.

b.) More particularly, the object of this invention is to enable the user to merely insert a special six axis radial type rotary-brush head-assembly into one's wide open mouth, close down the mouth slightly, switch on the motor's electrical-circuit, and experience a thorough 20-second omnioral-action (simultaneous cleaning of the entire upper and lower dental/gum array) brushing proceedure, which is a vigorous and simultaneous all around brushing, obviating need for indulgence of skillful dexterity in manipulating an active rotary mouthpiece, since all of the dental surfaces are being brushed uniformly in a skillfully human-engineered manner, making this instrument also highly useful for injured, aged, or handicap persons finding vigorous movement of the forearm a difficult to impossible task.

c.) Another object of this invention is to set forth a plastic supporting structure and drive-train arrangement capable of rigidly maintaining the relatively critical alignment relationship of the rotating brush members, while imposing a minimal amount of structural-mass which would tend to make the dental-instrument clumsy or awkward to insert and use within the user's mouth.

d.) another object of this invention is to set forth a dental brushing instrument which is made according to the proceeding criteria, yet at once made so as to be variably adjustable (human-engineered) to the different jaw/cranial widths among narrow to wide spans, as may be measured for example from the extreme lateral right to the extreme lateral left of one's molars. The object being, to enable the user to virtually adjust the inter-molar lateral span only but once upon initial use, whereupon the instrument will maintain this manually set span for the life of the instrument. Accordingly, it is desirable that this Y-shaped portion of the instrument be made facilely detachable from the substantially cylindrical handle portion, so as to thereby enable other family members to simply snap-on their own suitably adjusted brushing-unit (also for hygienic purposes).

e.) Another object of this invention is to set forth a special combination of six co-rotating radial-brush elements, arranged so that when viewed in axial cross-section the fifth and sixth define the central if primary-axis member, while the other four driven abaxial brush members would appear at the tips of an imaginary superimposed X-pattern which would serve to make up what is referred to as the gearing-cluster within the third-stage cluster-housing at the distal end of the Y-shaped bifurcated fork like supporting structure.

f.) Another object of this invention is to set forth an electric-toothbrush driving apparatus preferably cordless energizing via a conventional storage-battery; wherein is preferably included a second-stage gearingoutput (which may involve gear-speed reduction) such as via pinion-gears driving two divergent primary output-spindles operating within a rigid Y-shaped arrangement of cantilevering support-arm members. The two primary second-stage shafts are thus distally provided with axially elongated radial-brush elements serving only to essentially scrub the top surfaces of both the jaw & cranial molars; including a spur-gear (or equivalent driving means such as an O-ring belt or quad-ring type driving arrangement) at its extreme forward end region (that is, innermost region relative to open mouth insertion).

g.) Another object of this invention is to set forth an electric-toothbrush driving arrangement substantially according to proceeding example-#f, wherein is further included an arrangement of four cross-linked (or cross-coupled secondary driving-shafts, as follow: 1.) an upper/outside-shaft & brush driven by the right-hand/primary-shaft member, which loops around in a U-shaped formation to drive the upper/left-outside radial-brush portion as well; 2.) a lower/inner-shaft & brush, driven by the same right-hand/primary-shaft, which likewise loops around in an albeit tighter U-shaped formation to drive the lower/left-inside radial-brush potion as well; 3.) an upper/inside-shaft & brush, driven by the left-hand/primary-shaft, which loops around in a tight U-shaped formation to drive the upper/right-inside radial-brush portion as well; and, 4.) a lower/outside-shaft & brush driven by the same left-hand/primary-shaft, which also loops around in a U-shaped formation so as to drive the lower/right-outside radial-brush portion. Naturally, this unique over-and-under arrangement of cross-coupled driving-shafts may be optionally designed in a mirror-image manner for example; the essential object here being to achieve a novel simultaneous radial-brushing action described as "downward from the gum-surface, toward the tooth-surface" at virtually all four wrap-around dental-array surface regions: that is specifically, upper-outer, upper-inner, lower-outer, lower-inner. Thus, in unique combination with the aftward top & bottom molar surface brushing action of the two separate right & left driving-shaft brushes, an aggregate total brushing action is described which virtually reaches all of the vital dental brushing surfaces;

h.) another object of this invention is to set forth an electric-toothbrush drive-train substantially according to proceeding paragraphs-#e, f, g, wherein is included special miniature right & left transfer/gearing-cases which are supported at the extreme distal end of the right & left driving shafts, in order to achieve this well cantilevered drive-system configuration. Note that a thin hollow metal shaft housing uniquely contains both an inner co-axial primary/drive-shaft and an additional hollow outer co-axial sleeve-like radial-brushes. Hence, thereby enabling the right & left said primary-shafts to serve the additional task of driving the two abbreviated molar top-surface brushes as well. The purpose here also is to preferably specify a slightly formable material (such as a ductile alloy or malleable plastic) which would enable the user to manually bend the bifurcations so as to alter the span (lateral width), and thereby relocate the right & left molar top-surface scrubbing brushes directly over the center of the molars; thus, automatically aligning the four respective outer and inner rotary-brush members precisely at their proper positions, when the lower dental array is in close proximity with the upper dental array for effective scrubbing action against the inside and outside of the aggregate dental array for some 95% of the public.

DESCRIPTION OF THE PREFERRED EMBODIMENT DRAWINGS

The foregoing and still other objects of this invention will become fully apparent, along with various advantages and features of novelty residing in the present embodiments, from study of the foregoing description of the variant generic species embodiments and study of the ensuing description of these embodiments, wherein indica of reference are shown to match related points given in the text, as well as the Claims-section annexed hereto; and accordingly, a better understanding of the invention and the variant uses is intended, by reference to the drawings, which are considered as primarily exemplary and not to be therefore construed as restrictive in nature.

FIG. 1, is a pictorial view of the overall invention.

FIG. 2, is a plan-view of the FIG. 1 embodiment which has been swung around 180-degrees placing the handle portion at the right, and wherein a partial cut-away reveals preferred placement of the major component members therein.

FIG. 3, is an approximate 4× cross-sectional enlargement of one of the bifurcated brush portions as is indicated 3:3 is FIG. 2, including reference to regions of the mouth in cross-section for visual orientation.

FIG. 4, is an approximate 2½-enlargement detail of the special concentric-drive axis and annular brush arrangement poised between the teeth of FIG. 3, including a 90°/radial-quadrant thereof which is shown in cut-away manner for greater clearity.

FIG. 5, is a cross-sectional view of a brush segment shown in FIG. 3, which axis is merely rotated down 90-degrees while a portion of the brush is shown removed for greater spatial clarity.

FIG. 6, is a semi-diagramatic representation of the brushing array as it would appear through the lens of a wide-angle camera stationed near the apex of the U-shaped array.

NOMENCLATURE REFERENCES

| | |
|---|---|
| 10 | is the invention overall |
| 11/11'/11" | handle-body(+upper/lower ends) |
| 12 | handle extension/gear-housing |
| 13 | thumb-switch button |
| 14/14'/14" | bifurcated-extension(+right/left portions) |
| 15'/15" | right/left cluster-housing covers |
| 16'/16" | right/left cluster-housings |
| 17 | lower-outer rotary-brush |
| 18 | upper-outer rotary-brush |
| 19 | lower-inner rotary-brush |
| 20 | upper-inner rotary-brush |
| 21 | rechargable storage battery |
| 22 | d.c.elect.-motor |
| 23/23'/23" | motor/gear-housing, output-shaft, drive-gear |
| 24'/24" | right/left driven-gears(split) |
| 25'/25" | right/left split-driveshafts |
| 26/26'/26" | right/upper-outer driving-end members |
| 27/27'/27" | right/lower-inner driving-end members |
| 28/28'/28" | right/upper-inner driven-end members |
| 29/29'/29" | right/lower-outer driven-end members |
| 30/30' | right/sleeve-shaft & slip-gap |
| 31'/31" | right/left sleeve-shaft/rotary-brush |
| 32 | driveshaft slip-gap |
| 33 | O-ring drive-belt |
| 34 | drive-pully |
| 35 | driven-pully |
| 40 | jaw molar-tooth crown |
| 41 | ref./2nd.stage driver |
| 42 | jaw gum-tissue |

| | -continued |
|---|---|
| 43 | tongue |
| 44 | cheek-tissue |
| 45 | cranial gum-tissue |
| 46 | 3rd-stage/driven-end R.O.U. |
| 47 | 3rd-stage/driven-end R.I.L. |
| 48 | 3rd-stage/driving-end R.I.U. |
| 49 | 3rd-stage/driving-end R.O.L. |
| 50 | cranial molar-tooth crown |

DETAILED DESCRIPTION OF THE INVENTION AND PREFERRED EMBODIMENTS

Reference to the illustration of FIG. 1 shows the overall invention configuration 10 wherein is provided a handle 11 of about 1-inch nominal diameter, having a back-end 11", and a forward-end 11' which preferably joins contiguously with the forward-end transfer-case 12 which may include an underside electric/control-switch 12' (of the simple on/off single-pole/single-throw type). Here, a junction is preferably made coupling the said end portion 12 with the detatchable brush supporting structure 14 having bifurcated extension portions 14' (right) and 14" (left), which feature special cooperating members, as are to be explained. Also note, that the terms lateral right/left gives reference herein to the invention as it would be oriented while inserted in one's mouth; hence, the user's own right/left during use serves to determine such reference. Positioned most distally on the cantilevering forks 14'/14" are the respective cluster-housings 15'/15" from which the four individual radial-bristled U-shaped rotary-brush members 17, 18, 19, 20, are operating.

Study of FIG. 2 reveals the basic inner-workings of the proceeding embodiment, wherein is included a conventional storage-battery 21, permanent-magnet d.c./motor 22, motor gear-reduction housing 23 and attendant output-shaft 23' and shaft/pinion-gear 23". Note how the special gear configuration 24'/24" facilitates a very compact, however rugged arrangement, whereby the drive is split into two individual output-spindles 25'/25" which are preferably made of 0.025"-guage/stainless-wire which allows them to convey ample torque while routing forward within the said respective fork like arms 14'/14" into the said respective cluster-housings 15'/15" affixed thereto.

Notice now in FIG. 3 where an enlarged view of the cluster-housing 15' reveals how the said drive-shaft 25' ultimately drives three individual rotary-brush units 26", 27", and 31; and that the drive-shaft 25' is made square at it's end region (ref. FIG. 5) so as to receive the slip-on pully member 34 having a concentric sleeve-like return extension portion 30 (ref. cross-section of FIG. 4) precisely fitted thereto via a positive axial indexing tab, while also supporting an array of radial-bristles 31 thereto. The fork-arm 14' is preferably reduced in diameter here so that a critically compact dimensional relationship is achieved, and the cluster-housings are made so that the outer cover 15' member also acts as the outer pilot-bearing, which is joined in support by a similar bearing hole for a journal protrusion on the pully 34. Therefore, the aggregate cluster-housing is easily assembled at the factory, and easily accessed via snap-on cover 15', and is intended to run dry of any lubricant, since the components are preferably engineered of non corrosive materials, and the friction-drive O-ring 33/33' is likewise unlubricated. Note here also, that this is a typical cross-section example of preferred cluster-housing/support-arm (C-H/S-A) construction, whereby the driven-pully 35 is similarly constructed (albeit without a secondary sleeve like part 30), and is tantamount to a 3rd-stage drive-output which is uniquely cross-coupled in a U-shaped manner around to an identically constructed support-arm of cluster-housing 16" associated with the other cantilevered fork-arm 14". Note however, that where the 3rd-stage drive-shaft portion 26 enters the opposite C-H/S-A, there is preferably no additional pully member; thus the terminus of shaft 26 while well supported in a similar bearing-hole (as with arrangement of FIG. 5), only spins there in a freely idling manner, since it is positively driven from the opposite C-H/S-A.

Thus, it is understandable from the examples of FIGS. 3, 5, 6 how the aggregate rotary-brushes of FIG. 6 are simultaneously driven preferably all at the same rate, so as to revolve in their proper directions. Accordingly, it is alright that both the sleeve-drives 30/30' (on opposite fork-arms respectively) rotate in the exemplified clockwise manner, since they serve only to scrub the outermost crown region surfaces of exemplified molars 40 & 50. However, it is important to note that the other four semi-floating brush members 17, 18, 19, 20, are made to brush the dental debris outward from the spaces interjacent to the exemplified teeth 40/50 and the gums 42/45 respectively; as is demonstrated via the rotational/indicating-arrows of FIG. 3. Accordingly, FIG. 6 also serves to clearly identify in a semi-diagramatic manner the relationships of the four different 3rd-stage driven and cantilevered driving members. For example, the right/outer upper (ROU) driven portion is situated at region 46, the right/inner-lower (RIL) driven portion is situated at region 47, while the right-/inner-upper (RIU) driving portion is situated at region 48, and the right/outer-lower driving portion is situated at region 49.

Reference back to FIG. 2 reveals another important provision of this unique toothbrush instrument, whereby the arrows with reference BN (bend-narrower) shows how the cantilevered fork-arms 14'/14" may be manually squeezed toward one-another (or conversely, spread apart slightly) just enough to accomodate the various lateral jaw-width interval differences among the different end users. This is achieved through use of a sufficiently ductile structural material for the bifurcation 14. Finally, it is is intended that the bifurcated-housing portion 14 preferably include a substantially conventional arrangement of rapid snap-on attach-/detach entities, or other equivalent provision of substantially conventional design such as via magnetic means, facilitating convenient substitution of different brushing head units 14 from the handle body portion 11/12, in a manner conventionally known to plastic component construction, so that individual family members may quickly and easily attach their own custom-bent mouth brushing-unit 14 for example.

Lastly, it is understood that the utility of the foregoing adaptations of this invention are not dependent upon any prevailing invention patent necessarily; and while the present invention has been well described hereinbefore by way of several preferred embodiments, it is to be realized that various changes, alterations, rearrangements, and obvious modifications may be resorted to by those skilled in the art to which it relates, without substantially departing from the implied spirit and scope of this invention. Therefore, the invention has been disclosed herein by way of example and not via any thus imposed limitation.

What is claimed of proprietary inventive origin is:

1. An electric toothbrush for brushing an entire dental array inside and outside from the gums outwardly in a single operation, said toothbrush comprising; a rigid elongated housing defining a first housing portion forming a handle, an electric motor means, battery power means for said motor and switch means to control operation of said motor means mounted in said first housing portion, said motor means having a forwardly extending shaft means having gear means mounted thereon, a second housing portion extending forwardly from said first housing portion and having a bifurcated extension in the form of Y-shaped supporting means defined by forwardly extending arms, each said arm having mounted on the free end thereof an X-shaped drive housing defining two upwardly extending and two downwardly extending leg portions, a flexible drive shaft extending through each arm from adjacent the motor shaft gear means to said drive housing on the end of said arm, a gear means on one end of each said flexible shaft engaging said motor gear means and a drive means mounted on the other end of each said flexible shaft with one of each said drive means mounted in one of said drive housings, each said first drive means having sleeve means attached thereto and extending rearwardly toward the first housing portion, said sleeve means being mounted on the exterior of the respective arm, radial bristle means mounted on each said sleeve means and defining first cylindrical brush means, first upper and lower cylindrical brush means having first flexible shaft means and each said first flexible shaft means extending between said first and second drive housings and forming U-shaped brush arrangements above and below said arms, second upper and lower cylindrical brush means having second flexible shaft means shorter than said first flexible shaft means and each said second flexible shaft means extending between the first and second drive housing forming a U-shaped brush arrangement above and below said arms and forming with said first upper and lower cylindrical brush means a space between said upper cylindrical brush means and said lower cylindrical brush means for reception of upper and lower dental arrays, each of said drive housings having driven means mounted in the ends of the upwardly extending leg portions and one of the downwardly extending leg portions and bearing means mounted in the ends of the other leg portions such that one end of each said upper and lower cylindrical brush flexible shaft means is driven by said driven means and the other end is mounted in one of said bearing means, means drivingly connecting said drive and driven means to rotate said first and second upper and lower cylindrical brush means, whereby said first cylindrical brush means serves to brush the tops of upper and lower molars and said U-shaped upper and lower cylindrical brush arrangements clean the inside and outside of upper and lower dental arrays.

2. An electric toothbrush according to claim 1, wherein said bifurcated arms are made of a suitably ductile material, thereby enabling manual adjustment of the spacing interval between said arms, to suit any given user's lateral jaw width.

3. An electric toothbrush according to claim 1, wherein said second housing portion includes detatchable means, thus enabling instant removal of said second housing from said first housing portion; thereby facilitating convenient substitution of different brush head units.

* * * * *